US011725186B2

(12) United States Patent
Soon-Shiong et al.

(10) Patent No.: US 11,725,186 B2
(45) Date of Patent: Aug. 15, 2023

(54) RECOMBINANT NK CELLS EXPRESSING CO-STIMULATORY MOLECULES

(71) Applicant: NANT HOLDINGS IP, LLC, Culver City, CA (US)

(72) Inventors: Patrick Soon-Shiong, Culver City, CA (US); Kayvan Niazi, Encino, CA (US); Shahrooz Rabizadeh, Los Angeles, CA (US)

(73) Assignee: Nant Holdings IP, LLC, Culver City, CA (US)

(*) Notice: Subject to any disclaimer, the term of this patent is extended or adjusted under 35 U.S.C. 154(b) by 799 days.

(21) Appl. No.: 16/702,275

(22) Filed: Dec. 3, 2019

(65) Prior Publication Data

US 2020/0109366 A1 Apr. 9, 2020

Related U.S. Application Data

(62) Division of application No. 15/366,838, filed on Dec. 1, 2016, now Pat. No. 10,533,157.

(60) Provisional application No. 62/262,867, filed on Dec. 3, 2015.

(51) Int. Cl.
| | |
|---|---|
| *A61K 35/17* | (2015.01) |
| *C12N 5/0783* | (2010.01) |
| *A61K 39/00* | (2006.01) |
| *A61K 45/06* | (2006.01) |
| *C07K 14/735* | (2006.01) |
| *C07K 14/725* | (2006.01) |
| *C07K 16/30* | (2006.01) |
| *C07K 14/715* | (2006.01) |
| *C12N 15/85* | (2006.01) |

(52) U.S. Cl.
CPC .......... *C12N 5/0646* (2013.01); *A61K 35/17* (2013.01); *A61K 39/0011* (2013.01); *A61K 45/06* (2013.01); *C07K 14/7051* (2013.01); *C07K 14/70535* (2013.01); *C07K 14/715* (2013.01); *C07K 16/30* (2013.01); *C12N 15/85* (2013.01); *A61K 2039/5156* (2013.01); *A61K 2039/572* (2013.01); *C07K 2317/622* (2013.01); *C07K 2319/70* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,618,817 | B2 | 11/2009 | Campbell |
| 10,533,157 | B1 | 1/2020 | Soon-Shiong et al. |
| 2015/0079088 | A1 | 3/2015 | Lowman et al. |
| 2016/0045551 | A1 | 2/2016 | Brentjens et al. |

OTHER PUBLICATIONS

Vigneron et al., "Database of T cell-defined human tumor antigens: the 2013 update", Cancer immunity, Jul. 15, 2013, vol. 13, 6 pages (Cited from Specification).
Garnett et al., "TRICOM Vector Based Cancer Vaccines", Current Pharmaceutical Design, 2006, vol. 12, No. 3, pp. 351-361.
Niazi et al., "Activation of human CD4+ T cells by targeting MHC class II epitopes to endosomal compartments using human CD1 tail sequences", Immunology, vol. 122, pp. 522-531 (Cited from Specification).
NK-92 (ATCC CRL-2407), accessed by https://www.atcc.org/products/all/CRL-2407.aspx?&p=&rel=generalinformation#generalinformation, accessed at Aug. 14, 2019, 1 page.
Anikeeva et al., "Integrin receptors on tumor cells facilitate NK cell-mediated antibody-dependent cytotoxicity", Cellular immune response, Eur. J. Immunol., 2014, vol. 44, pp. 2331-2339.
Bakdash et al., "The nature of activatory and tolerogenic dendritic cell-derived signal II", Frontiers in Immunology, Antigen Presenting Cell Biology, Feb. 2013, vol. 4, No. 53, 18 pages.
Bartkowiak et al., "4-1BB agonists: multi-potent potentiators of tumor immunity", Front. in Oncol., Jun. 2015, vol. 5, No. 117, 16 pages.
Jarahian et al., "Blockade of natural killer cell-mediated lysis by NCAM140 expressed on tumor cells", Int. J. Cancer, 2007, vol. 120, pp. 2625-2634.
Long et al., "Controlling Natural Killer Cell Responses: Integration of Signals for Activation and Inhibition", Annu. Rev. Immunol., 2013, vol. 31. pp. 227-258.
Maki et al., "Factors Regulating the Cytotoxic Activity of the Human Natural Killer Cell Line, NK-92", Journal of Hematotherapy & Stem Cell Research, 2001, vol. 10, No. 3, pp. 369-383.
Maki et al., "Induction of sensitivity to NK-mediated cytotoxicity by TNF-α treatment: possible role of ICAM-3 and CD44", Leukemia, 1998, vol. 12, pp. 1565-1572.
Steblyanko et al., "Integrins Influence the Size and Dynamics of Signaling Microclusters in a Pyk2-dependent Manner", The Journal of Biological Chemistry, May 8, 2015, vol. 290, No. 19, pp. 11833-11842.
Suck et al., "KHYG-1 and NK-92 represent different subtypes of LFA-1-mediated NK cell adhesiveness", Frontiers in Bioscience E3, Jan. 1, 2011, pp. 166-178.
Weitzman et al., "Variable Contribution of Monoclonal Antibodies to ADCC in patients with chronic lymphocytic Leukemia", Leukemia & Lymphoma, vol. 50, No. 8, pp. 1361-1368.
Zhang et al., "Characterization of interleukin-15 gene-modified human natural killer cells: implications for adoptive cellular immunotherapy", haematologica, Mar. 2004, vol. 89, No. 3, pp. 338-347.
Zhang et al., "Characterization of stem cell factor gene-modified human natural killer cell line, NK-92 cells: Implication in NK cell-based adoptive cellular immunotherapy", Oncology Reports, 2004, vol. 11, pp. 1097-1106.
Non-Final Office Action received for U.S. Appl. No. 15/366,838, dated Jan. 25, 2019, 48 pages.
Final Office Action received for U.S. Appl. No. 15/366,838, dated Jun. 18, 2019, 48 pages.
Notice of allowance received for U.S. Appl. No. 15/366,838, dated Sep. 5, 2019, 48 pages.

*Primary Examiner* — Marcia S Noble
(74) *Attorney, Agent, or Firm* — Martin Fessenmaier; Umberg Zipser LLP

(57) ABSTRACT

Cancer immunotherapy using genetically engineered NK cells is enhanced by expression of recombinant co-stimulatory molecules to deliver co-stimulatory signals to a recipient host's immune cells to enhance an immune response.

20 Claims, 1 Drawing Sheet

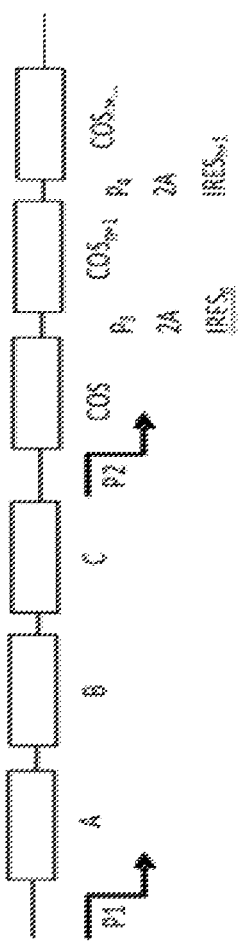

RECOMBINANT NK CELLS EXPRESSING CO-STIMULATORY MOLECULES

This application is a divisional application of allowed U.S. patent application with the Ser. No. 15/366,838, filed Dec. 1, 2016, which claims priority to U.S. Provisional Application 62/262,867, filed Dec. 3, 2015.

FIELD OF THE INVENTION

The field of the invention is treatment of neoplastic diseases, and especially as they relate to prophylaxis and treatment of neoplastic diseases using recombinant natural killer (NK) cells.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

It is well known that most, if not all neoplastic diseases are accompanied by a relatively large number of cellular DNA mutations, including point mutations, insertions, deletions, and translocations. Thus, it is reasonable to assume that neoplastic cells should also be characterized by the presence of one or more mutated proteins. Unfortunately, and despite such a simple premise, the search for mutated proteins that are suitable for diagnosis and therapy has been complicated by the fact that different cancer types have different mutated proteins, and worse yet, different patients with the same tumor type have vastly different reservoirs of mutated proteins.

More recently, as a result of numerous research efforts, a relatively small collection of T-cell defined human tumor antigens has become available (see e.g., Cancer Immunity (15 Jul. 2013) Vol. 13, p. 15), however, these antigens have not resulted in a single effective therapeutic agent. Additionally, the use of these antigens in immunotherapy is conceptually questionable, because these antigens are already present in a patient diagnosed with cancer, and should have given rise to an appropriate immune response. Moreover, even if tumor specific antigens are identified and used in a cancer vaccine, the immune response to such antigens may not be sufficiently strong to elicit a therapeutic effect.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In particular, an effective immune therapy requires activated T-cells and activated NK cells to allow specific and rapid destruction of cancer cells. However, while many epitopes associated with or specific to a tumor can be readily processed and even recognized by selected components of the immune system (e.g., by dendritic cells, certain T-cells), a therapeutically effective response by the immune system is often not achieved, possibly due to downregulation of cytotoxic T-lymphocytes and/or NK cells. To counteract downregulation, immune checkpoint inhibitors can be administered to a patient, and some of these therapeutic approaches have shown promise in the clinic (e.g., targeting CTLA-4 or PD-1). However, such approach has not proven universally applicable or even therapeutically effective in most cancers and immune therapy.

The expression of a tumor-associated antigen in genetically engineered T-cells is known. For example, a pox virus has been genetically altered to force infected cells to co-express a tumor associated antigen together with co-stimulatory molecules to so potentially increase an immune response against a tumor carrying the tumor associated antigen (Curr Pharm Des. 2006; 12(3):351-61). However, although co-expression using pox virus was at least conceptually promising, clinical results may be less than desirable as the stimulated immune response could still be reduced by various endogenous factors, and because pox viruses are typically immunogenic and will be eradicated by the patient's immune system.

Thus, while numerous immune therapeutic compositions and methods are known in the art, all or almost all of them suffer from various disadvantages. Therefore, there is still a need for improved compositions and methods that allow for a therapeutically effective immune response in treatment of various cancers.

SUMMARY OF THE INVENTION

The inventive subject matter is drawn to compositions, modified cells, and methods of enhancing cancer immune response by using genetically engineered NK cells that express one or more recombinant co-stimulatory molecules.

One aspect of the inventive subject matter provides for a genetically engineered natural killer (NK) cell with a recombinant nucleic acid encoding at least a portion of at least one co-stimulatory molecule. In some aspects of the inventive subject matter, it is contemplated that the genetically engineered natural killer cell can be an immortalized cell, for example a genetically engineered NK92 cell.

With respect to the natural killer cell, it is contemplated that in some embodiments the natural killer cell is genetically engineered to have a reduced or abolished expression of at least one killer cell immunoglobulin-like receptor (KIR). Preferably, the KIR comprises two domains. It is also contemplated that in some aspects, the natural killer cell can be genetically engineered to express a high-affinity Fcγ receptor, for example a FcγIII receptor. Alternatively, or additionally, the Fcγ receptor can be coupled to an antibody which has binding specificity against a tumor associated antigen, a tumor specific antigen, and/or a cancer neoepitope.

It is further contemplated that in some aspects of the inventive subject matter, the natural killer cell can be genetically engineered to express a chimeric T-cell receptor. Preferably, the chimeric T-cell receptor can contain an scFv portion. Alternatively, or additionally, it is contemplated that the chimeric T-cell receptor can have an ectodomain with binding specificity against a tumor associated antigen, a tumor specific antigen, and/or a cancer neoepitope.

With respect to the co-stimulatory molecule, it is contemplated that in some embodiments that the co-stimulatory molecule comprises all or part of one or more of the following molecules: B7.1 (CD80), B7.2 (CD86), ICAM-1 (CD54), ICOS-L, LFA-3 (CD58), 4-1BBL, CD30L, CD40, CD40L, CD48, CD70, CD112, CD155, GITRL, OX40L, and/or TL1A.

While not limiting to the inventive subject matter, it is further contemplated that the recombinant nucleic acid may further encode a cytokine. Preferably, the cytokine can be IL-2, IL-12 and/or IL-15. Furthermore, it is contemplated in some aspects that the recombinant nucleic acid can comprise a regulatory element which allows non-constitutive expression of the co-stimulatory molecule(s).

Another aspect of the inventive subject matter is directed toward a method of modifying a genetically engineered NK cell by introducing a recombinant nucleic acid encoding at least a portion of at least one co-stimulatory molecule into the genetically engineered NK cell. In another step, the modified genetically engineered NK cell is cultured in a first medium to a desired NK cell quantity. In yet another step, the first medium is replaced with a second medium which suitable for injection of the modified genetically engineered NK cells into a patient.

While not limiting the inventive subject, in some aspects the method of targeting an NK requires an immortalized NK cell and/or a genetically engineered NK92 cell. It is further contemplated that in some aspects the NK cell can be (a) genetically engineered to have a reduced or abolished expression of at least one killer cell immunoglobulin-like receptor (KIR), (b) genetically engineered to express a high-affinity Fcγ receptor, and/or (c) genetically engineered to express a chimeric T-cell receptor.

Furthermore, in some aspects of the method, the introduced nucleic acid can encode for one or more of the following co-stimulatory molecules: B7.1 (CD80), B7.2 (CD86), ICAM-1 (CD54), ICOS-L, LFA-3 (CD58), 4-1BBL, CD30L, CD40, CD40L, CD48, CD70, CD112, CD155, GITRL, OX40L, and/or TL1A. It is further contemplated that in some aspects the recombinant nucleic acid further encodes a cytokine.

The inventor contemplates further aspects of pharmaceutical compositions comprising a genetically engineered NK cell describe in the composition or method above. In some aspects the pharmaceutical composition also contains an immune checkpoint inhibitor. Furthermore, the pharmaceutical composition can be prepared according to the method described above.

In yet another aspect of the inventive subject matter, the inventor contemplates a method of treating a patient with cancer by administering a genetically engineered NK cell as described above to under a protocol effective to provide the genetically engineered NK cell to a tumor in the patient. In some aspects, the method comprises a further step of administering an immune checkpoint inhibitor as part of the treatment method.

Finally, the inventor also contemplates use of a genetically engineered NK cell as described above to reduce the tumor cell burden in a patient having a tumor. In some aspects of the contemplated use, the genetically engineered natural killer cells can be injected into the patient's tumor. Additionally, or alternatively, the genetically engineered NK cells can be co-administered to the patient with an immune checkpoint inhibitor. In some aspects, the inventor contemplates the manufacture of a medicament to treat a tumor cell in a patient containing the genetically engineered NK cells. Preferably, the medicament can be formulated for injection.

Various objects, features, aspects and advantages of the inventive subject matter will become more apparent from the following detailed description of preferred embodiments, along with the accompanying drawing FIGURES in which like numerals represent like components.

BRIEF DESCRIPTION OF THE DRAWING

FIG. 1 illustrates an exemplary recombinant nucleic acid coding for more than one co-stimulatory molecule.

DETAILED DESCRIPTION

The inventors have now discovered that the efficacy of immunotherapeutic compositions can be improved by equipping NK cells to present co-stimulatory molecules. In particularly preferred aspects of the inventive subject matter, the NK cells are genetically engineered to achieve one or more desirable traits, and/or are continuously growing, or 'immortalized'. By presentation of the co-stimulatory molecules on the surface of the NK cells it is believed that the so modified cells will exhibit dendritic cell characteristics with respect to T-cell activation, while retaining killing activity via NK cell-specific pathways.

The genetically engineered NK cells will most preferably be activated NK cells (aNKs), high-affinity NK cells (haNKs), and/or target activated NK cells (taNKs). It should be appreciated that all NK cells are deemed suitable, from various possible sources. In many aspects, preferred NK cells will be autologous (e.g. patient-derived). The NK cells can be directly isolated from blood or stem cells from the same patient. However, in some preferred embodiments, the NK cells are allogenic and continuously growing, or "immortalized," so that they can be cultured and multiplied outside of the patient.

Although also contemplated, heterologous NK cells are less preferred. In cases where the genetically-modified NK cell is desired to be available on a commercial scale, heterologous NK cells can be immortalized. Furthermore, where a genetically-modified NK cell is desired to present for only a short time, the NK cell may be irradiated prior to delivery into the body so as to prevent the NK cell's ability to further multiply.

In one particularly preferred aspect of the inventive subject matter, the genetically engineered NK cell can be a NK-92 derivative and is modified to have a reduced or abolished expression of at least one killer cell immunoglobulin-like receptor (KIR), which will render such cells constitutively activated (via lack of or reduced inhibition). Therefore, suitable modified cells may have one or more modified killer cell immunoglobulin-like receptors that are mutated such as to reduce or abolish interaction with MHC class I molecules. Of course, it should be noted that one or more KIRs may also be deleted, or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest as aNK cells ('activated natural killer cells). Such cells may then be further modified to express the co-stimulatory molecules as further discussed below.

In another preferred aspect of the inventive subject matter, the genetically engineered NK cell may also be an NK-92 derivative that is modified to express the high-affinity Fcγ receptor (CD16). Sequences for high-affinity variants of the Fcγ receptor are well known in the art, and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells ('high-affinity natural killer cells). Such cells may then be further modified to express the co-stimulatory molecules as further discussed below.

In one exemplary aspect of the inventive subject matter, genetically engineered NK cells may be used to influence the immune response to a tumor. While not wishing to be bound by any theory or hypothesis, it is contemplated that a patient's T-cell is bound to a tumor cell, but the T-cell has been inactivated. Upon contact of the genetically engineered NK cell with the tumor, and due to the expression of co-stimulatory molecules on the genetically engineered NK cell, the presence of the genetically engineered NK cell is thought to (re)activate the T-cell, which allows a cytotoxic response of the T-cell to so eliminate the tumor cell. In this manner, the genetically engineered NK cell can help prevent or reverse the formation of inactive or anergic T-cells. In an alternative scenario, the genetically engineered NK cell can aid in the recruitment and activation of T-cells by exhibiting dendritic-cell like properties (e.g. the expression of co-stimulatory molecules, or the response to tumor associated antigen via MHC-I and MHC-II pathways on the NK cell). In yet another example, the genetically modified NK cell is thought to aid a dendritic cell in the activation of a T-cell by ensuring an appropriate concentration of co-stimulatory molecules, which in turn may facilitate proper formation of an activating immune synapse. In yet another scenario, it is thought that the genetically engineered NK cells could initiate an immune response by other immune competent cells following the NK cell mediated killing of a tumor cell. Such killing initiates an immune cascade in which the resulting tumor associated antigens or neoepitopes are released and presented via dendritic cells (via the MHC-1 or MHC-2 pathway), that are then able to activate T-cells. It should be appreciated that the above examples are for illustrative purposes only and do not encompass all contemplated examples.

In yet a further aspect of the inventive subject matter, the genetically engineered NK cell may also be genetically engineered to express a chimeric T-cell receptor. In especially preferred aspects, the chimeric T-cell receptor will have an scFv portion or other ectodomain with binding specificity against a tumor associated antigen, a tumor specific antigen, and/or a cancer neoepitope. As noted before, there are numerous manners of genetically engineering an NK cell to express such chimeric T-cell receptor, and all manners are deemed suitable for use herein. Alternatively, such cells may also be commercially obtained from NantKwest as taNK cells ('target-activated natural killer cells'). Such cells may then be further modified to express the co-stimulatory molecules as further discussed below.

Where the cells are engineered to have affinity towards a cancer associated antigen or antibody with specificity towards a cancer associated antigen, it is contemplated that all known cancer associated antigens are considered appropriate for use. For example, cancer associated antigens include CEA, MUC-1, CYPB1, etc. Likewise, where the cells are engineered to have affinity towards a cancer specific antigen or antibody with specificity towards a cancer specific antigen, it is contemplated that all known cancer specific antigens are considered appropriate for use. For example, cancer specific antigens include PSA, Her-2, PSA, brachyury, etc. Where the cells are engineered to have affinity towards a cancer neoepitope or antibody with specificity towards a cancer neoepitope, it is contemplated that all known manners of identifying neoepitopes will lead to suitable targets. For example, neoepitopes may be identified from a patient tumor in a first step by whole genome analysis of a tumor biopsy (or lymph biopsy or biopsy of a metastatic site) and matched normal tissue (i.e., non-diseased tissue from the same patient) via synchronous comparison of the so obtained omics information. So identified neoepitopes can then be further filtered for a match to the patient's HLA type to increase likelihood of antigen presentation of the neoepitope. Most preferably, such matching can be done in silico.

Regardless of the particular type of genetically engineered NK cell (e.g., patient-derived NK cell, aNK, haNK, or tank), it is generally preferred that the cells are further transformed with a recombinant nucleic acid construct that is suitable for (inducible) expression of at least one co-stimulatory molecule. For example, suitable co-stimulatory molecules are selected from the group consisting of B7.1 (CD80), B7.2 (CD86), ICAM-1 (CD54), ICOS-L, and LFA-3 (CD58). Further contemplated co-stimulatory molecules include 4-1BBL, CD30L, CD40, CD40L, CD48, CD70, CD112, CD155, GITRL, OX40L, LIGHT, TIM3, TIM4, and TL1A. Moreover, it should be appreciated that expression of the co-stimulatory molecules will preferably be coordinated such that a genetically modified NK cell will have at least two or three co-stimulatory molecules expressed on the cell surface. For example, suitable recombinant nucleic acids will include sequences that encode B7.1 (CD80), B7.2 (CD86), ICAM-1 (CD54), and ICOS-L, and/or that encode two or more co-stimulatory molecules selected form the group consisting of 4-1BBL, CD30L, CD40, CD40L, CD48, CD58, SLAM, TIM4, TIM1L, HVEM, LIGHT, CD70, CD112, CD155, GITRL, OX40L, and TL1A. Thus, it should be appreciated that the so prepared NK cells may act in a dendritic cell fashion with respect to T-cell activation while also providing granzyme activity to the diseased cells. Finally, where desired, treatment may also include administration of immune checkpoint inhibitors to further enhance or stimulate a robust immune response. Moreover, it should be noted that the genetically engineered cells may not only express a co-stimulatory molecule, but also its normally occurring binding partner. For example, where the genetically engineered NK cell expresses OX40L, OX40 may be co-expressed and may thus be co-presented on the cell surface. Likewise, where the genetically engineered NK cell expresses B7-1 and/or B7-2, CD28 may be co-expressed and may thus be co-presented on the cell surface. Of course, it should be appreciated that the recombinant nucleic acid may be constructed such that co-expression of the receptor and ligand may result in two distinct polypeptides, or that receptor and ligand are expressed as a single polypeptide (with an optional linker between the receptor and the ligand).

Moreover, it should also be appreciated that multiple different cell populations may be prepared that have different combinations or sub-combinations of co-stimulatory molecules to so even further increase the anticipated therapeutic effect. Where desired, it is also contemplated that these cells may further include one or more sequence elements in the recombinant nucleic acid that encode an immune stimulatory cytokine, and especially preferred immune stimulatory cytokines include IL-2, IL-12 and IL-15 (or IL-15 superagonist or ALT803), which may be expressed from the same or different recombinant nucleic acid in a coordinated or independent manner.

In still further contemplated aspects, it should be appreciated that many suitable methods may be employed to genetically engineer NK cells to give them dendritic cell-like properties. For example, methods which result in a permanent change in the cell may be used, for example genome editing via CRISPR/Cas9. More transient methods may include insertion of an extra chromosomal nucleic acid (e.g. plasmid), which may be delivered via infection by a viral vector or lipofection, poration (e.g., electroporation, sonoporation, photoporation via cavitation. Preferably, the extra nucleic acid is a single RNA, but may be single stranded or double stranded DNA as well. It should also be appreciated that the above methods can be altered using promoter elements known in the art to constitutively express the added nucleic acid or inducibly express the added nucleic acid when desired. For instance, in some cases it may be preferred to employ a hypoxia-sensitive promoter to induce expression of the nucleic acid in the hypoxic conditions of the tumor micro-environment.

FIG. 1 illustrates one example of how suitable recombinant nucleic acids may be configured. Here, two independent transcripts are formed from the recombinant nucleic acid starting from two typically identical promoter sequences P1 and P2. The first transcript in this example has three segments encoding three distinct neoepitopes (and/or immune stimulating cytokines) A, B, and C, while the second transcript has three segments encoding co-stimulatory molecules, B7.1 (CD80), ICAM-1 (CD54), and LFA-3 (CD58). Of course, it should be appreciated that first and second transcripts need not be separate transcripts but may be a single transcript from a single common promoter. Likewise, it should be appreciated that the transcript need not have (or have less) sequence elements that encode for neoepitopes and/or immune stimulatory cytokines, and that the number of segments encoding the neoepitopes and/or co-stimulatory molecules may also vary considerably. Thus, the co-stimulatory molecules encoded in the three segments of the second transcript need not be limited to three, but may be one or two, or four, five, six or even more. While it is generally preferred that the co-stimulatory molecules will be distinct (e.g., LFA-3, ICAM-1, B7.1, B7.2, or ICOS-L), it is noted that at least two may also be the same. In still further contemplated aspects, it should also be appreciated that each of the segments may have its own promoter sequence to allow for individual expression, or two segments may share an IRES (internal ribosome entry site) or 2A sequence (cleavable 2A-like peptide sequence). Alternatively, individual promoter sequences (P3, P4, . . . ) may also be employed.

With respect to the expressed co-stimulatory molecules it is generally preferred that the molecules will include a native or chimeric domain that directs the protein into the membrane of the NK cell such that the expressed co-stimulatory molecules are presented at the outer surface of the cell. There are numerous suitable transmembrane domains known in the art, and all of those are deemed suitable for use herein. However, especially preferred domains include the native domains that are already present in the co-stimulatory molecules. For example, transmembrane domains may be derived from CD3, CD28, and/or CD8. Most typically, the transmembrane domain will not include an activating or inhibitory domain (e.g., ITAM or ITIM).

It should further be appreciated that other sequences are also contemplated. For example, as shown in FIG. 1, in some embodiments sequences A, B, and C may encode for at least one chemokine, or other entity (e.g., membrane-bound antibody or antibody fragment) that targets the genetically engineered cell to a cancer cell. Moreover, it should be appreciated that the recombinant nucleic acid construct may direct the expressed neoepitope towards the MHC-I and/or MHC-II pathway. This allows for the cells to display a tumor antigen via MHC-I and/or MHC-II pathways similar to a dendritic cell. With respect to the integration of sequence portions that encode the neoepitopes it should be noted that the various neoepitopes may be arranged in numerous manners, and that a transcription or translation unit may have concatemeric arrangement of multiple epitopes, typically separated by short linkers (e.g., flexible linkers having between 4 and 20 amino acids), which may further include protease cleavage sites. Such concatemers may include between 1 and 20 neoepitopes (typically limited by size of recombinant nucleic acid that can be delivered via a virus), and it should be noted that the concatemers may be identical for delivery to the MHC-I and MHC-II complex, or different. Therefore, and as noted below, it should be appreciated that various peptides can be routed to specific cellular compartments to so achieve preferential or even specific presentation via MHC-I and/or MHC-II. Viewed from another perspective, it should be recognized that tumor associated antigens and neoepitopes may be presented via both presentation pathways, or selectively to one or another pathway at the same time or in subsequent rounds of treatment.

It is contemplated that where expression of more than one neoepitope is preferred, for example two, three, four, five, and even more, expression can be accomplished using multiple distinct genetically modified NK cells having more than one neoepitope sequence (e.g., as concatemeric or chimeric sequence). While not limiting to the inventive subject matter, it is generally preferred that neoepitope sequences are configured as a tandem minigene (e.g., $aa_{12}$-neoepitope$_{12}$-$aa_{12}$), or as single transcriptional unit, which may or may not be translated to a chimeric protein. Thus, it should be appreciated that the epitopes can be presented as monomers, multimers, individually or concatemeric, or as hybrid sequences with N- and/or C-terminal peptides. Most typically, it is preferred that the nucleic acid sequence is back-translated using suitable codon usage to accommodate the virus and/or host codon preference. However, alternate codon usage or non-matched codon usage is also deemed appropriate. With respect to further suitable configurations and expression cassettes reference is made to co-pending US provisional applications with the Ser. No. 62/302,168, filed Mar. 2, 2016, and the Ser. No. 62/314,366, filed Mar. 28, 2016, both incorporated by reference herein.

As noted above neoepitope sequences (e.g., expressed as single neoepitope or as polytope) may be configured and directed to one or both MHC presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmatic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane. Thus, expression of the epitopes intended for MHC-II presentation will generally be directed to the endosomal and lysosomal compartment as is also discussed in more detail below.

In most preferred aspects, signal peptides may be used for trafficking the neoepitopes to the endosomal and lysosomal compartment (and with directing the neoepitope presentation towards MHC-II), or for retention in the cytoplasmic space (and with directing the neoepitope presentation towards MHC-I). For example, where the peptide is to be exported to the endosomal and lysosomal compartment targeting presequences and the internal targeting peptides can be employed. The presequences of the targeting peptide are preferably added to the N-terminus and comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[LI] or DXXLL consensus motifs. All of these signals are recognized by components of protein coats peripherally associated with the cytosolic face of membranes. YXXØ and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology*, 122, 522-531).

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

Recombinant nucleic acids will further include a sequence portion that encodes one or more antagonistic peptide ligands that bind to a checkpoint receptor. Most typically, binding will inhibit or at least reduce signaling via the receptor, and particularly contemplated receptors include CTLA-4 (especially for CD8+ cells) PD-1 (especially for CD4+ cells). For example, peptide binders can include antibody fragments and especially scFv, but also small molecule peptide ligands that specifically bind to the receptors. Once more, it should be appreciated that expression of the peptide molecules will preferably be coordinated such that the antigens and/or neoepitopes are presented on the cell surface of the NK cell along with one or more peptide molecules. Thus, it is typically contemplated that the peptide molecules are produced from a single transcript, for example, using an internal ribosome entry site or 2A sequence, or from multiple transcripts.

Most typically, expression of the recombinant genes is driven from constitutively active regulatory sequences. However, in other aspects of the inventive subject matter, the regulatory sequences may be inducible, preferably in a selective manner using one or more regulatory signals endogenous to the cancerous tissue or synthetic inducers. In most cases, it is further preferred that the transcript will includes an IRES (internal ribosome entry site) or a 2A sequence (cleavable 2A-like peptide sequence) to again allow for coordinated expression of the cytokines and co-stimulatory molecules.

Thus, modified NK cells may then be used in a pharmaceutical composition, typically formulated as a sterile injectable composition with between $10^4$-$10^{11}$ cells, and more typically $10^5$-$10^9$ cells per dosage unit. However, alternative formulations are also deemed suitable for use herein, and all known routes and modes of administration are contemplated herein. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

In addition, it is contemplated that prophylactic or therapeutic administration of the NK cells may be accompanied by co-administration with immune checkpoint inhibitors to reduce possible inhibitory action on T-cells. For example, especially preferred check point inhibitors include currently available inhibitors (e.g., pembrolizumab, nivolumab, ipilimumab) under the same protocol and dosage as prescribed. Alternatively, suitable inhibitors also include those that target PD-1, CTLA-4, or other receptors that, upon ligand binding, downregulate T-cell activity. Moreover, it should be recognized that the NK cells may be administered as adjuvant to a chemotherapy regimen.

It should be appreciated that other methods that do not involve genetically modifying the NK cell are contemplated. For example, it is possible to graft the desired co-stimulatory molecules directly onto a target NK cell, as opposed to coercing the NK cell to produce the co-stimulatory molecules. For example, liposomes and/or exosomes could be prepared with the appropriate co-stimulatory molecules, and then the liposomes/exosomes are incubated with the NK cells such that the liposomes/exosomes fuse with the NK cell membrane and the co-stimulatory molecules are present on the NK cell membrane. For example, fusion may be encouraged by acidic pH and/or polyethylene glycol. Alternatively, membrane fragments of genetically modified NK cells may be fused with liposomes to so generate hybrid exosomes. In still another example, it is contemplated that an antibody that specifically binds to NK cell markers could be modified to carry a co-stimulatory molecule. NK cells could be incubated with the antibody, which would result in the co-stimulatory molecules being presented on the outside of the NK cells. Additionally, or alternatively, such other methods may be used in conjunction with genetic modification.

Finally, it should be appreciated that it may desirable to prevent NK cells from becoming exhausted. Thus, it contemplated that NK cells can be engineered or overexpressed according to the methods outlined above to overexpress 4-1BB and/or 4-1BBL to maintain durability of the NK cells. Therefore, 4-1BB and/or 4-1BB ligand encoding sequences may be included in the recombinant nucleic acids.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a patient having a cancer, comprising:
   administering a genetically engineered natural killer cell to the patient;
   wherein the genetically engineered natural killer cell includes a recombinant nucleic acid that comprises
   a first promoter region operably linked to at least three coding sequences, each encoding a neoepitope or an immune stimulating cytokine; and
   a second promoter region operably linked to at least three coding sequences, each encoding at least a portion of at least one co-stimulatory molecule.

2. The method of claim 1 further comprising a step of administering an immune checkpoint inhibitor.

3. The method of claim 1 further comprising a step of administering an immune stimulating cytokine.

4. The method of claim 1 further comprising a step of administering chemotherapy to the patient.

5. The method of claim 1 wherein the natural killer cell is genetically engineered to have a reduced or abolished expression of at least one killer cell immunoglobulin-like receptor (KIR).

6. The method of claim 1 wherein the natural killer cell is genetically engineered to express a high-affinity Fcγ receptor.

7. The method of claim 6 wherein the Fcγ receptor is coupled to an antibody and wherein the antibody has binding specificity against a tumor associated antigen, a tumor specific antigen, and a cancer neoepitope.

8. The method of claim 1 wherein the natural killer cell is genetically engineered to express a chimeric T-cell receptor.

9. The method of claim 8 wherein the chimeric T-cell receptor comprises an scFv portion, and wherein the chimeric T-cell receptor has an ectodomain with binding specificity against a tumor associated antigen, a tumor specific antigen, and a cancer neoepitope.

10. The method of claim 1 wherein the at least one co-stimulatory molecule is selected from the group consisting of B7.1 (CD80), B7.2 (CD86), ICAM-1 (CD54), ICOS-L, LFA-3 (CD58), 4-1BBL, CD30L, CD40, CD40L, CD48, CD70, CD112, CD155, GITRL, OX40L, and TL1A.

11. The method of claim 10 wherein the at least one of the three coding sequences that are operably linked to the first promoter region encodes the immune stimulating cytokine.

12. The method of claim 11 wherein the cytokine is IL-2, IL-12, IL15, an IL-15 superagonist, and/or ALT803.

13. The method of claim 1 wherein the recombinant nucleic acid further comprises a regulatory element to allow inducible expression of the at least one co-stimulatory molecule.

14. The method of claim 1 wherein the at least one of the three coding sequences that are operably linked to the first promoter region encodes the neoepitope.

15. The method of claim 1 wherein the recombinant nucleic acid further comprises a segment that directs the at least one neoepitope towards MHC-I or MHC-II presentation.

16. The method of claim 1 wherein the genetically engineered natural killer cell is irradiated prior to administration.

17. The method of claim 1 wherein the recombinant nucleic acid is an RNA.

18. The method of claim 1 wherein the recombinant nucleic acid encodes an IRES (internal ribosome entry site) or a 2A sequence (cleavable 2A-like peptide sequence).

19. The method of claim 1 wherein the genetically engineered natural killer cells are administered at a dosage of $10^4$-$10^{11}$ cells per dosage unit.

20. The method of claim 1 wherein the genetically engineered natural killer cells are administered at a dosage of $10^5$-$10^9$ cells per dosage unit.

* * * * *